(12) United States Patent
Recanati et al.

(10) Patent No.: US 10,945,803 B2
(45) Date of Patent: Mar. 16, 2021

(54) CABLE, WIRE AND TUBE ORGANIZER FOR LAPAROSCOPIC AND HYSTEROSCOPIC SURGERY

(71) Applicants: Maurice Andre Recanati, New York, NY (US); Mohammad Ali Ozbeki, Novi, MI (US); Hanna G. Ozbeki, Novi, MI (US)

(72) Inventors: Maurice Andre Recanati, New York, NY (US); Mohammad Ali Ozbeki, Novi, MI (US); Hanna G. Ozbeki, Novi, MI (US)

( * ) Notice: Subject to any disclaimer, the term of this patent is extended or adjusted under 35 U.S.C. 154(b) by 0 days.

(21) Appl. No.: 16/844,839

(22) Filed: Apr. 9, 2020

(65) Prior Publication Data

US 2020/0253681 A1    Aug. 13, 2020

Related U.S. Application Data

(60) Continuation-in-part of application No. 16/594,654, filed on Oct. 7, 2019, now abandoned, which is a
(Continued)

(51) Int. Cl.
*A61B 50/20*    (2016.01)
*F16L 3/10*     (2006.01)
*F16L 3/223*    (2006.01)

(52) U.S. Cl.
CPC ............ *A61B 50/20* (2016.02); *F16L 3/1075* (2013.01); *F16L 3/2235* (2013.01)

(58) Field of Classification Search
CPC ....... A61B 50/20; A61B 46/23; E02F 9/2257; H02G 3/32; F16L 3/223; F16L 3/1075;
(Continued)

(56) References Cited

U.S. PATENT DOCUMENTS 2,902,821 A * 9/1959 Kelly, Jr. ............... A44C 5/102
                                                    59/80
3,519,981 A * 7/1970 Koletsos .................. H02G 9/10
                                                   439/798
(Continued)

FOREIGN PATENT DOCUMENTS

DE       2208752 A1 *  8/1973    ............ F16L 3/2235
DE       2208752 A1    8/1973
(Continued)

*Primary Examiner* — Kimberly T Wood
(74) *Attorney, Agent, or Firm* — Jacob M. Ward; Ward Law Office LLC

(57) ABSTRACT

An organizing device for use during medical procedures is disclosed which, when used during laparoscopic or hysteroscopic surgery, enables the surgeon to keep multiple tubes, wires and cables organized. In a first embodiment, this device may have a rectangular shaped body, a top section with an integral ring at its center and a bottom section having a plurality of slots optimized for the insertion and retention of cables and tubes. The end sections contain, on one end a second integral ring, and on another a pivot point allowing a friction-closure latch mechanism to secure the slots. In a second embodiment, the device may have a donut shaped body, an integral ring at the center and a plurality of slots radially arranged at the periphery and secured through a cylindrical latching mechanism. In a third embodiment, the device may be secured using magnets instead of a pivoting latch mechanism.

9 Claims, 15 Drawing Sheets

Related U.S. Application Data division of application No. 15/893,806, filed on Jan. 12, 2018, now Pat. No. 10,433,926.

(60) Provisional application No. 62/457,206, filed on Feb. 10, 2017.

(58) Field of Classification Search
CPC ..... F16L 3/2235; F16L 3/1083; F16L 3/1091; F16L 3/08; F16L 3/10; F16L 3/1025
USPC ..... 248/58, 62, 63, 64, 228.5, 230.5, 231.61
See application file for complete search history.

(56) References Cited

U.S. PATENT DOCUMENTS

| | | | |
|---|---|---|---|
| 4,579,310 A | 4/1986 | Wells et al. | |
| 4,660,790 A | 4/1987 | Muz | |
| 4,775,121 A | 10/1988 | Carty | |
| 4,881,705 A | 11/1989 | Kraus | |
| 5,060,810 A | 10/1991 | Jones | |
| 5,224,674 A | 7/1993 | Simons | |
| 5,240,224 A | 8/1993 | Adams | |
| 5,316,246 A | 5/1994 | Scott et al. | |
| 5,361,956 A | 11/1994 | Recanati | |
| 5,363,539 A | 11/1994 | Tisol | |
| 5,389,082 A | 2/1995 | Baugues | |
| D380,115 S | 6/1997 | Fairweather | |
| 5,653,411 A | 8/1997 | Picco et al. | |
| 5,742,982 A * | 4/1998 | Dodd | F16G 11/00 24/16 R |
| 5,836,130 A | 11/1998 | Unruh et al. | |
| 5,901,888 A | 5/1999 | Schneider | |
| 6,458,104 B2 | 10/2002 | Gautsche | |
| 8,020,259 B2 | 9/2011 | Ho et al. | |
| 8,141,722 B2 | 3/2012 | Heroux | |
| 8,261,482 B1 * | 9/2012 | Buchanan | A01K 77/00 206/223 |
| 8,408,501 B2 | 4/2013 | Noyes | |
| 8,708,290 B2 | 4/2014 | Franta | |
| 9,106,068 B2 * | 8/2015 | Barna | H02G 3/32 |
| 10,433,926 B2 | 10/2019 | Recanati et al. | |
| 2005/0109721 A1 | 5/2005 | Schneider | |
| 2005/0194057 A1 * | 9/2005 | Pappas | H02G 3/305 140/123 |
| 2009/0200434 A1 | 8/2009 | Noyes et al. | |
| 2010/0078036 A1 * | 4/2010 | Naji | A45D 8/12 132/200 |
| 2010/0159741 A1 * | 6/2010 | Rothbaum | F16G 11/00 439/501 |
| 2011/0084039 A1 | 4/2011 | Walters et al. | |
| 2011/0290951 A1 * | 12/2011 | Guthke | H02G 3/32 248/68.1 |
| 2012/0006947 A1 | 1/2012 | Gundel et al. | |
| 2013/0104667 A1 * | 5/2013 | Koyano | G01F 15/14 73/861.25 |
| 2013/0187012 A1 * | 7/2013 | Blakeley | H02G 3/32 248/68.1 |
| 2014/0245784 A1 * | 9/2014 | Proud | G06Q 40/04 63/1.11 |
| 2014/0374544 A1 | 12/2014 | Pearson et al. | |
| 2015/0265941 A1 * | 9/2015 | Scarborough | A63H 33/02 472/68 |
| 2016/0007697 A1 * | 1/2016 | de Jong | G06F 1/1637 361/679.03 |
| 2016/0053917 A1 | 2/2016 | Kean et al. | |
| 2020/0038131 A1 | 2/2020 | Recanati et al. | |

FOREIGN PATENT DOCUMENTS

| | | | | |
|---|---|---|---|---|
| DE | 102011009496 A1 | 8/2012 | | |
| DE | 102011009496 A1 * | 8/2012 | ............ | F16L 3/2235 |
| DE | 202016104525 U1 | 9/2016 | | |
| DE | 202016104525 U1 * | 9/2016 | ............ | F16L 3/2235 |
| GB | 399285 A * | 10/1933 | ............ | G16L 3/2235 |
| GB | 399285 A | 10/1933 | | |
| JP | H0684092 U * | 12/1994 | | |
| JP | H0684092 U | 12/1994 | | |
| JP | 2943864 B1 * | 8/1999 | ............ | F16L 3/2235 |
| JP | 2943864 B1 | 8/1999 | | |
| JP | 2000046244 A * | 2/2000 | ................ | F16L 3/14 |
| JP | 2000046244 A | 2/2000 | | |
| JP | 3710344 B2 | 10/2005 | | |
| JP | 3710344 B2 * | 10/2005 | | |
| WO | 0079660 A1 | 12/2000 | | |
| WO | WO-0079660 A1 * | 12/2000 | ................ | F16L 3/06 |
| WO | 2011097072 A1 | 8/2011 | | |
| WO | 2012101216 A1 | 8/2012 | | |
| WO | WO-2012101216 A1 * | 8/2012 | ............ | F16L 3/2235 |

* cited by examiner

CABLE, WIRE AND TUBE ORGANIZER FOR LAPAROSCOPIC AND HYSTEROSCOPIC SURGERY

CROSS-REFERENCE TO RELATED APPLICATIONS

This application is a continuation-in-part of U.S. Divisional patent application Ser. No. 16/594,654, filed Oct. 7, 2019, which in turn claims the benefit of U.S. patent application Ser. No. 15/893,806, filed on Feb. 12, 2018, and issued as U.S. Pat. No. 10,433,926 on Oct. 8, 2019, which in turn claims the benefit of U.S. Provisional Application No. 62/457,206, filed on Feb. 10, 2017. The entire disclosures of the above applications are hereby incorporated herein by reference.

FIELD

The present disclosure relates to a surgical instrument which facilitates conducting laparoscopic and hysteroscopic surgeries by organizing the cables going to the instruments on the surgical field.

BACKGROUND

The statements in this section merely provide background information related to the present disclosure and may not constitute prior art.

Minimally invasive surgery is becoming the most prevalent type of surgery performed in the United States. It allows for greater recovery times, minimizes the need for hospital admissions, minimizes scarring and affords greater safety, superior visualization and minimizes blood loss. Both laparoscopic pelvic surgery and hysteroscopic surgery utilize complex equipment, each of which requires a tube, cable or wire. For instance, the typical laparoscopic surgical field, while performing a hysterectomy, comprises of a video cable (for the operative camera), a light-cord cable (to illuminate the pelvis), a cautery cable (to cauterize bleeding) and a directed energy cable (for devices capable of cutting and sealing tissues). In addition, a gas tube (to create and maintain abdominal pneumoperitoneum), a twin tube for the laparoscopic suction and irrigator also course through the surgical field.

Oftentimes, these cables get tangled which may slow down the surgery or, occasionally, create situations that may potentially be dangerous to patients. Instruments which are not secured may fall to the ground or may dangle below the surgical drapes where they may become contaminated and potentially cause infection and sepsis. Being able to secure the cables and tubes is therefore critical to performing safe surgeries yet presently no device adequately addresses these problems.

In this domain, all the devices of the prior art have drawbacks, and are not readily accepted by surgeons for practical and safety issues. For example, International Patent Application Publication No. WO2011097072 and U.S. Patent Application Publication No. 20110084039, both to Walters et al., describe a device with clamps. However, the Walters et al. device cannot be mounted vertically for hysteroscopic surgery and the design of the clamps may damage delicate cables such as fiber optical light cables.

The U.S. Pat. No. 5,224,674 to Simons describes an apparatus for organizing intravenous fluid lines. However, the Simons device prevents tubes from sliding freely through its body and is too bulky to use within a crowded sterile field in the operating room. The U.S. Pat. No. 4,579,310 to Wells et al. describes an electrical guide for organizing wires. However, the Wells et al. device would be unsuitable for hollow tubes and would be difficult to secure to the surgical field.

There is a continuing need for a cable, wire and tube organizer for use during medical procedures such as surgery, and which offers solutions to overcome the many drawbacks of previous cable organizers and displays a number of desirable features.

SUMMARY

In concordance with the instant disclosure, a cable, wire and tube organizer for use during medical procedures such as surgery, and which offers solutions to overcome the many drawbacks of previous cable organizers and displays a number of desirable features, is surprisingly discovered.

In one embodiment, an organizing device for use during a medical procedure includes a donut shaped main body and a latching mechanism. The main body has a plurality of integral holders configured to secure at least one of a cable, a wire, and a tube during the medical procedure such as a surgery or operation. Each of the integral holders has at least one insertion slot with an inwardly tilted tooth for receiving the one of the cable, the wire, and the tube. The main body further has attachment means configured to secure the main body to a surgical field. The latching mechanism is pivotally attached to the main body and selectively movable between an open position and a closed position. The latching mechanism is configured to permit the insertion of the one of the cable, the wire, and the tube in the insertion slot when in the open position. The latching mechanism is also configured to occlude the insertion slots when in the closed position, and thereby secure the one of the cable, the wire, and the tube in the insertion slot.

In an exemplary embodiment, the organizing device includes a substantially flat main body with no separable parts, one or several integral rings, integral holders, and a latching mechanism.

The one or several integral rings are of sufficient strength for securing the device to the surgical field. The rings are integrally part of the main body of the device. The rings are capable of quickly securing the device and removing the device. The rings are capable of accepting hook-and-loop fastener (Velcro™) tabs, surgical towel clamps, or other means of securing the device to the surgical field. The rings allow the device to be mounted vertically or horizontally.

The integral holders of the device may be a plurality of holders that are integrally part of the main body of the device. The integral holders have an insertion slot wide enough to allow cables and an inwardly tilted tooth. The integral holders also have an area bounded by a resting surface, and the integral holder and the inwardly tilted tooth have a generally circular cross section. All surfaces of the integral holders have rounded contours, and are of sufficient size to accommodate cables and tubes typically used during laparoscopic and hysteroscopic surgery. The integral holders are also shaped to that inserted cables must negotiate a generally S-shaped path prior to resting on the resting surface.

The latching mechanism of the device may be capable of occluding the insertion slots of the integral holders. The latching mechanism may be retractable, and secured to the main body by a permanent fastener such as a rivet or other support. The latching mechanism may be secured from opening inadvertently through friction or by a fastener such as a cam latch.

In one example, the device is comprised of a substantially rectangular body. The substantially rectangular body has a top section with an integral ring at the center, a second integral ring, a bottom section, and a pivot point. The second integral ring is located at one end of the main body. The bottom section has a plurality of integrated holders. The pivot point permits attachment of a latching mechanism. The pivot point may have a U-shaped cross section and is secured to the main body through a fastener. The pivot point may have a friction closure mechanism preventing free movement.

The device may further have no separable parts. The main body and the latch may each be produced by injection molding. For example, the device may be composed of a general-purpose polypropylene copolymer. In another example, the device is composed of stainless steel. The means for connecting may also be provided in the form of a rivet. In certain examples, the friction mechanism may include grooves molded into the area about the pivot point. The plurality of hooks may be four (4), and in a most particular example may be six (6). Advantageously, the device is disposable, although in some instances the device may be sterilized for reuse.

In another example, the device is comprised of a substantially donut shaped body. The donut shaped body has a central integrated ring. The central integrated ring is hollow, and integrally molded in the main body of the device. The hollow portion of the central integrated ring is capable of accepting hook-and-loop fastener (e.g., Velcro™) tabs, surgical towel clamps, or other means of securing the device to the surgical field. The central integrated ring has radially arranged integral holders located along the outer perimeter of the main body and integrally part of the main body of the device. The central integrated ring also has a radial support allowing the retention of a cylindrical latch mechanism. The cylindrical latch is capable of occluding the insertion slots, and may include two identical half cylinders, a curvilinear cross section permitting a flush fit against the insertion slots, a hinge joining the two half cylinders to the radial support, and a cam latch catch allowing for fasteners to secure the two half cylinders together.

Several objects and advantages of the present invention are provided, namely: a) a device capable of accepting, retaining and organizing multiple cables wires and tubes; b) a mechanism allowing the cables to be secured to the device after insertion; c) a device capable of accepting tubes and wires of various diameters without scuffing or rubbing the insulation around them; d) a device capable of being secured either to the surgical drape itself, to an attachment on the mayo stand or to the IV poles at the head of the surgical field; e) a device which may be used for robotic, laparoscopic or hysteroscopic surgery; f) a device which may retain a bag containing surgical instruments which are not currently being used; g) a device which is flat and may sit flush with the surgical field; h) a device which may be sterilized; i) a device may be disposable; j) a device which may be injection molded; k) a device which is inexpensive to manufacture; l) a device which is safe to use and has no sharp angles; m) a device that has no loose or separable parts; n) a device that withstands the loads applied; and o) a device that is easy to use.

Further areas of applicability will become apparent from the description provided herein. It should be understood that the description and specific examples are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical unless otherwise disclosed.

Figure 1:
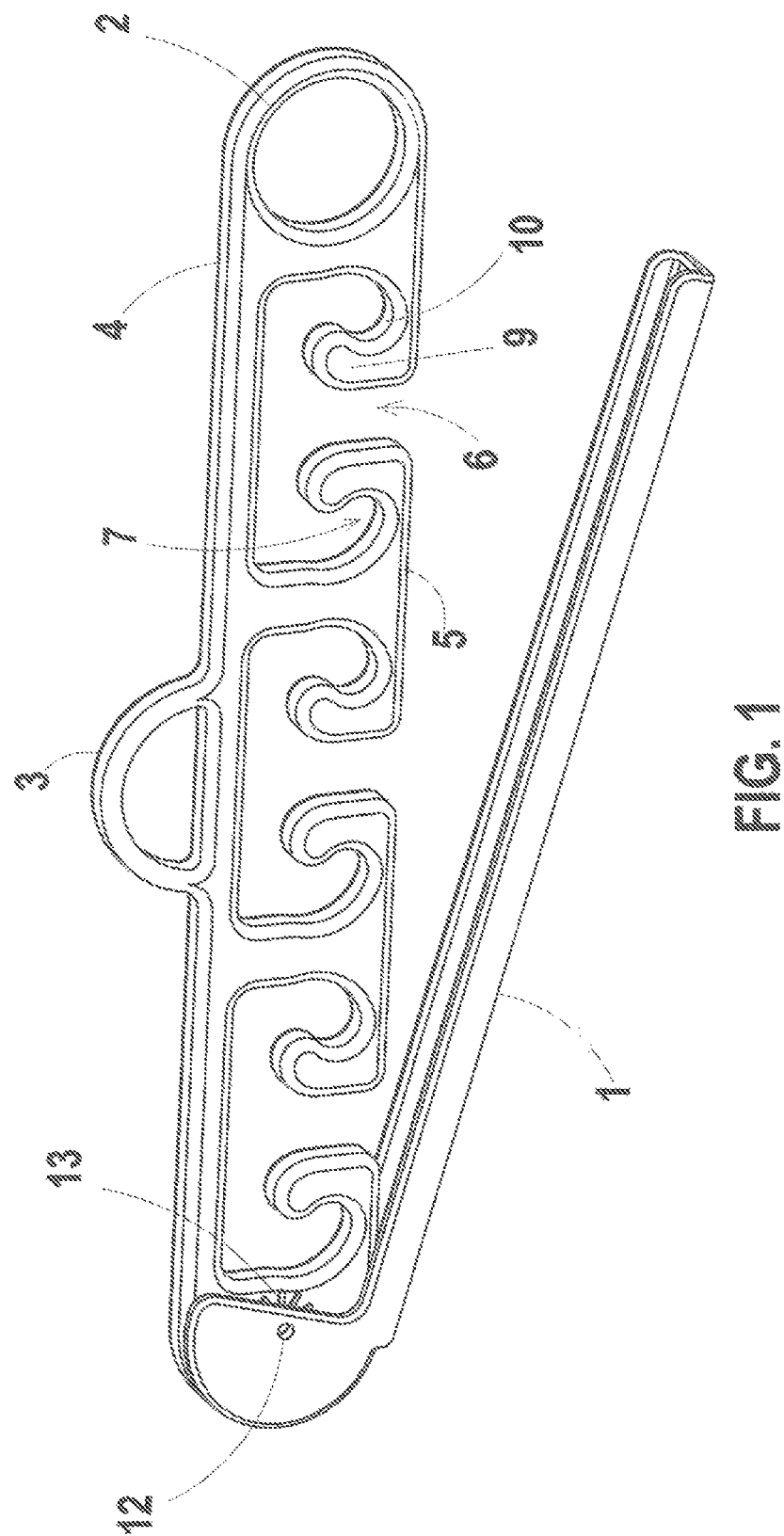
FIG. 1 is a top perspective view of a cable organizer according to one embodiment of the present disclosure, the cable organizer shown with a latch opened.
Figure 2:
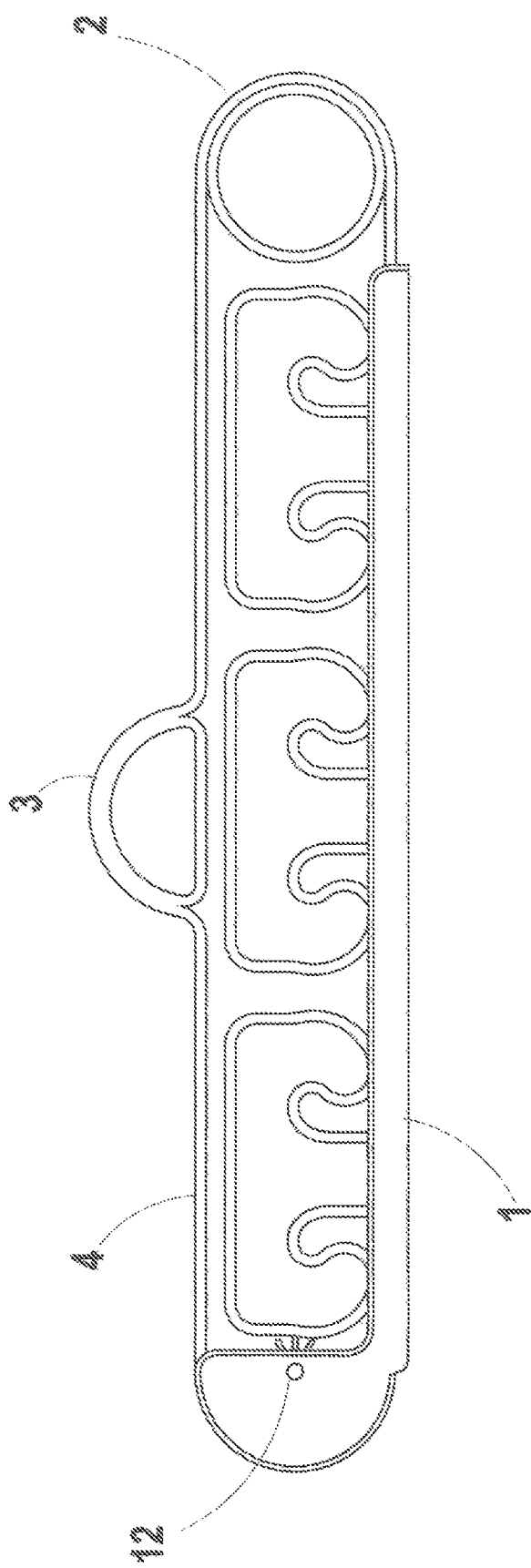
FIG. 2 is a side elevational view of the cable organizer of FIG. 1, the cable organizer shown with the latch closed.
Figure 3:
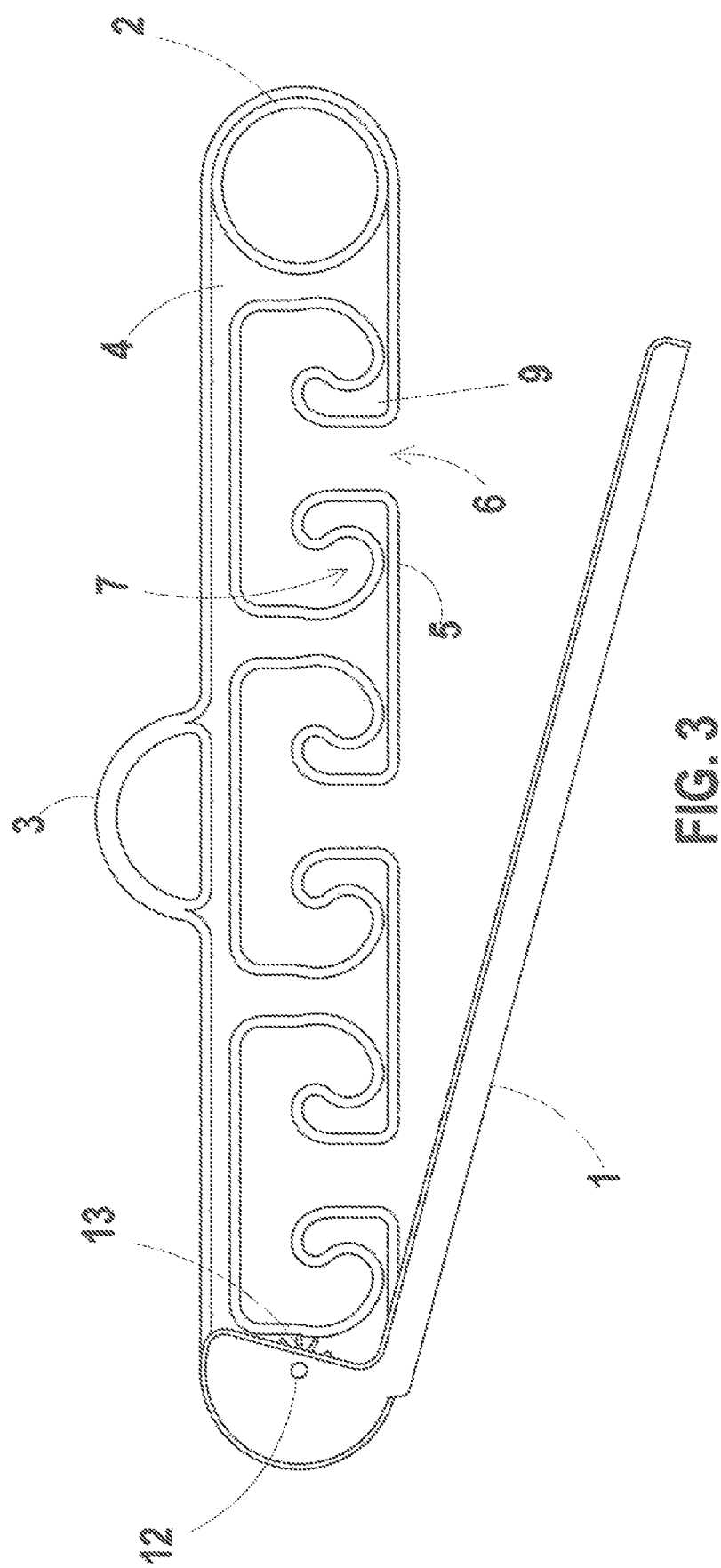
FIG. 3 is a side elevational view of the cable organizer of FIG. 1, the cable organizer shown with the latch opened.
Figure 4:
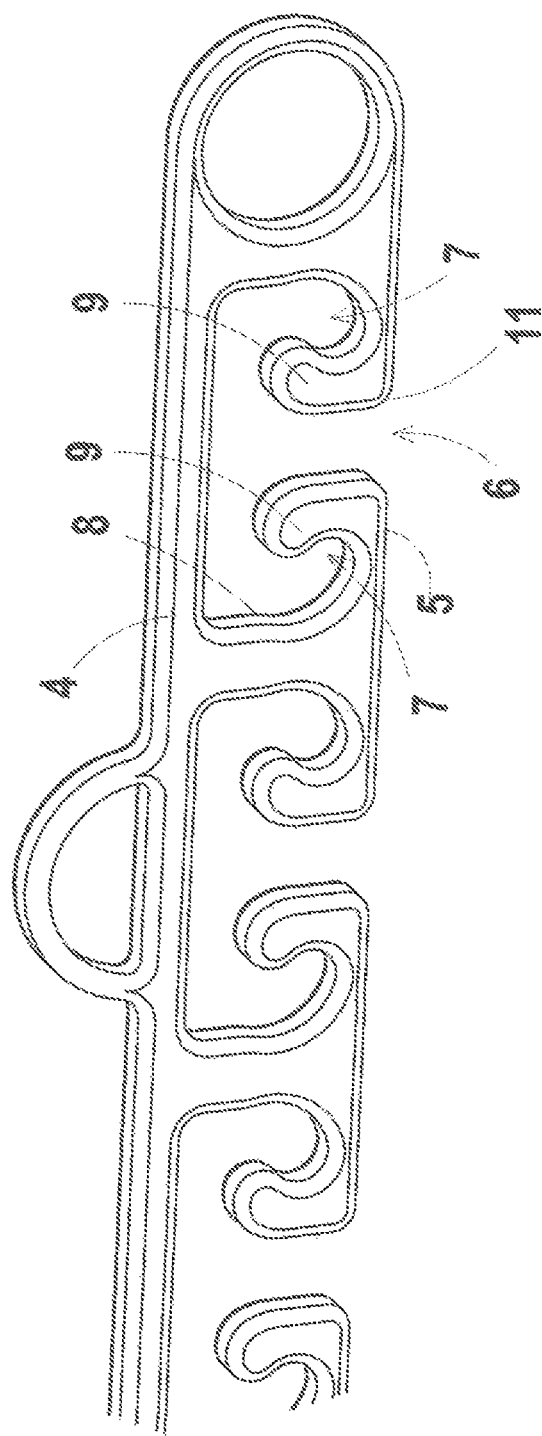
FIG. 4 is a partial, enlarged, top perspective view of a main body of the cable organizer of FIG. 1.
Figure 5:
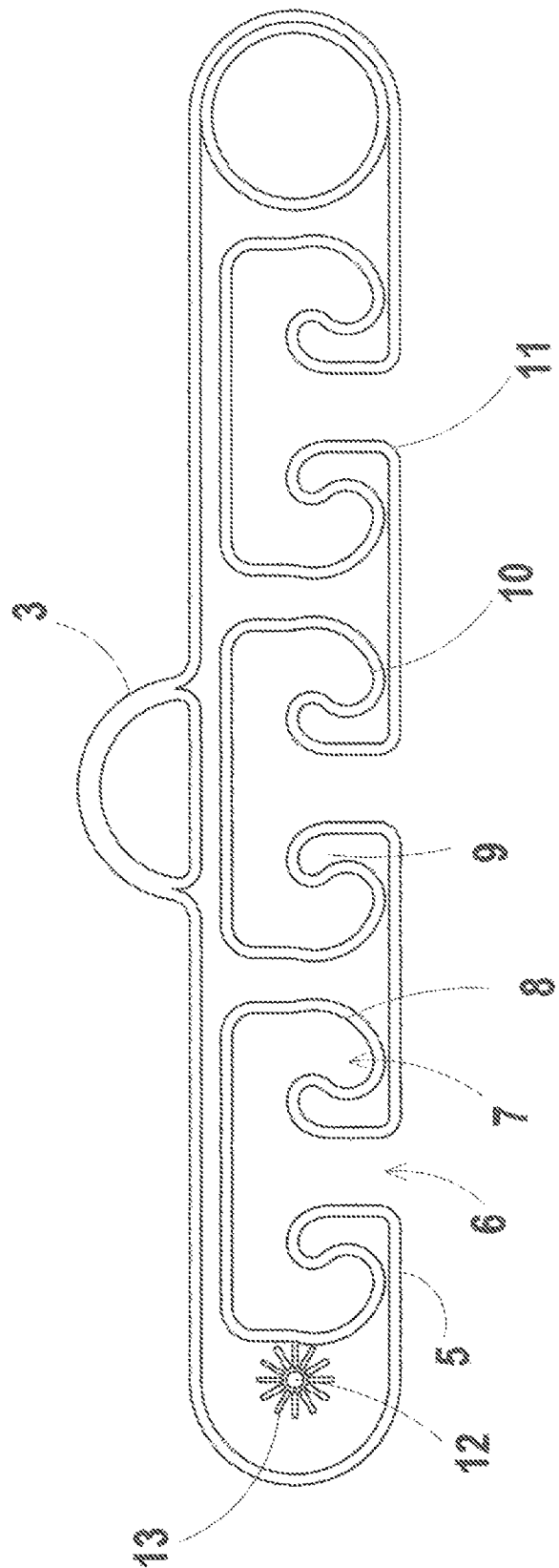
FIG. 5 is a side elevational view of the main body of the cable organizer of FIG.
Figure 6:
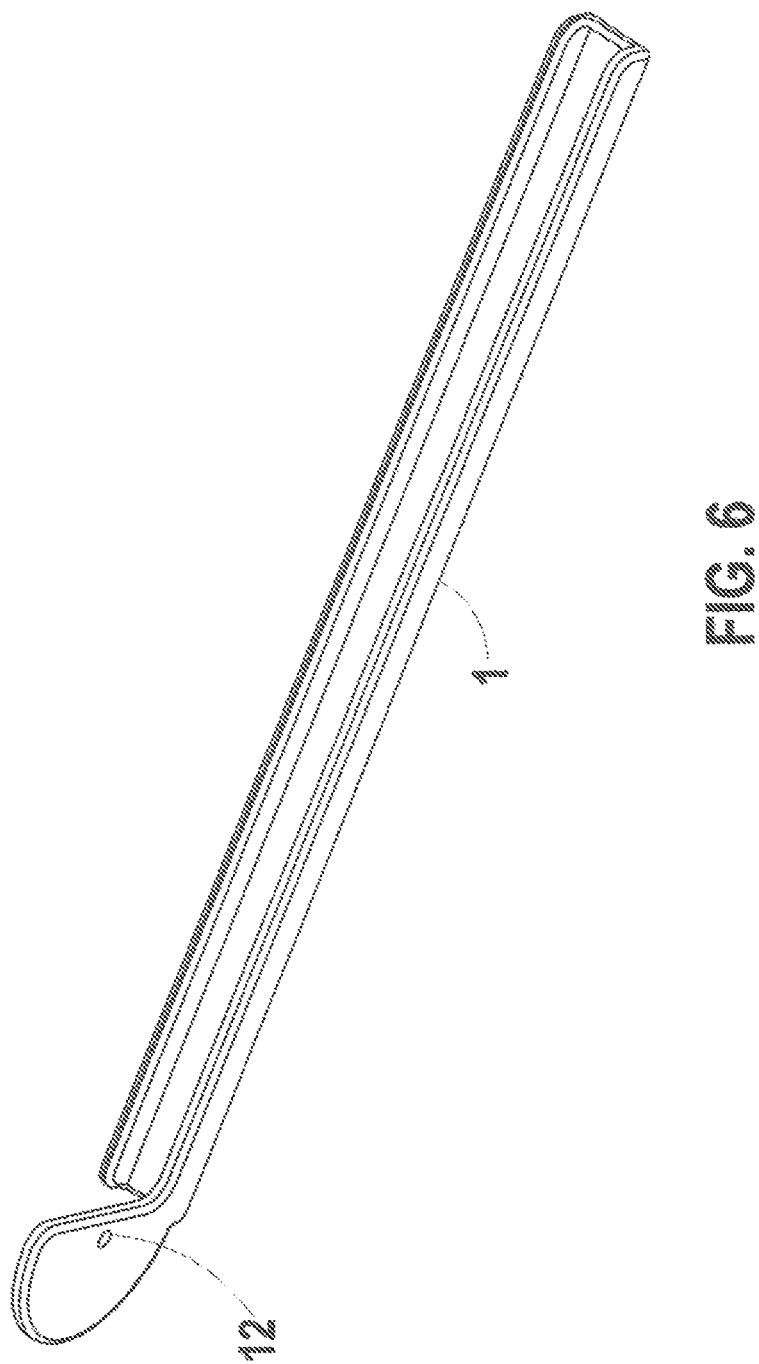
FIG. 6 is a top perspective view of the latch of the cable organizer of FIG. 1.
Figure 7:
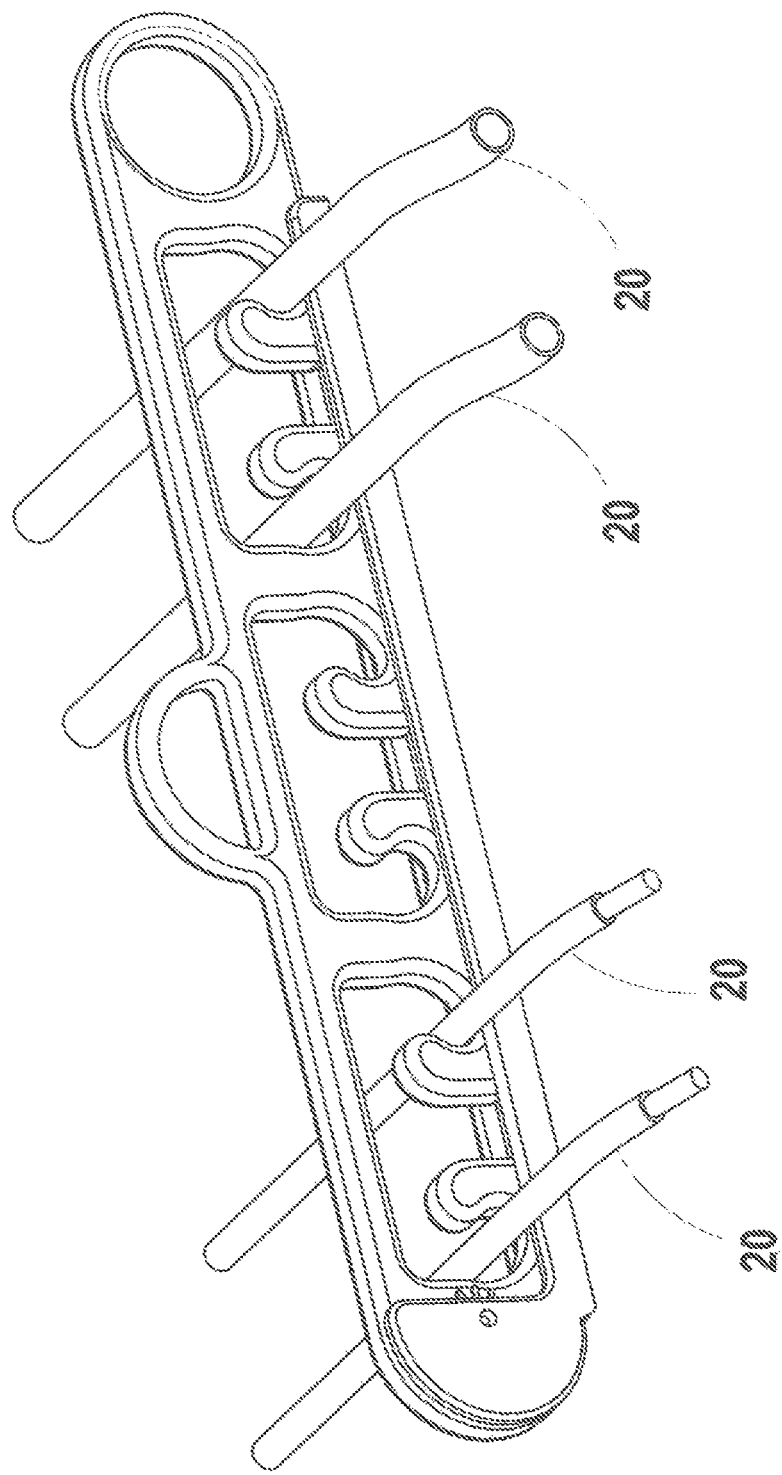
FIG. 7 is a top perspective view of the cable organizer of FIG. 1, the cable organizer shown in operation and securing cables.
Figure 8:
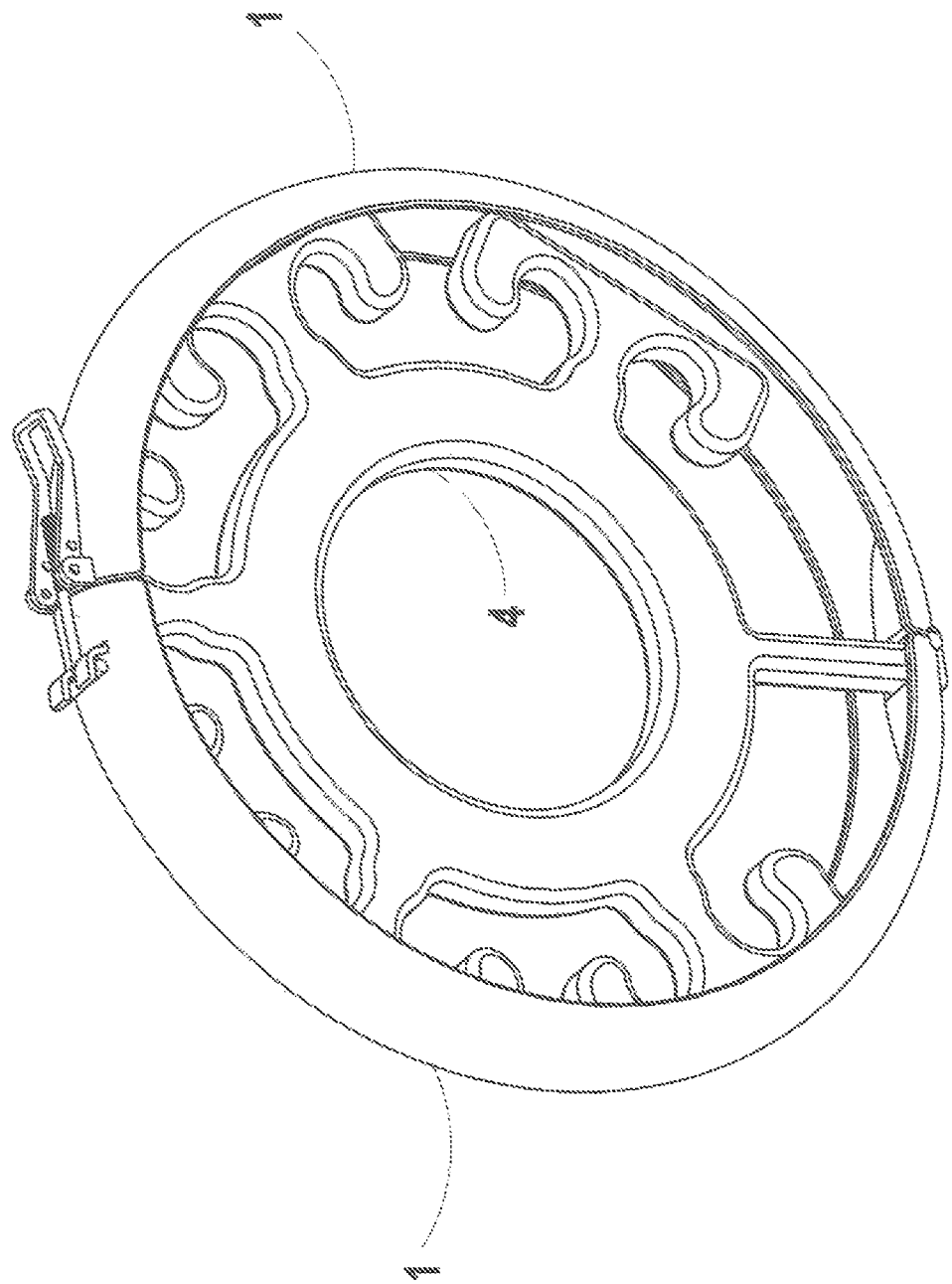
FIG. 8 is a top perspective view of a cable organizer according to another embodiment of the present disclosure, the cable organizer shown with latches closed.
Figure 9:
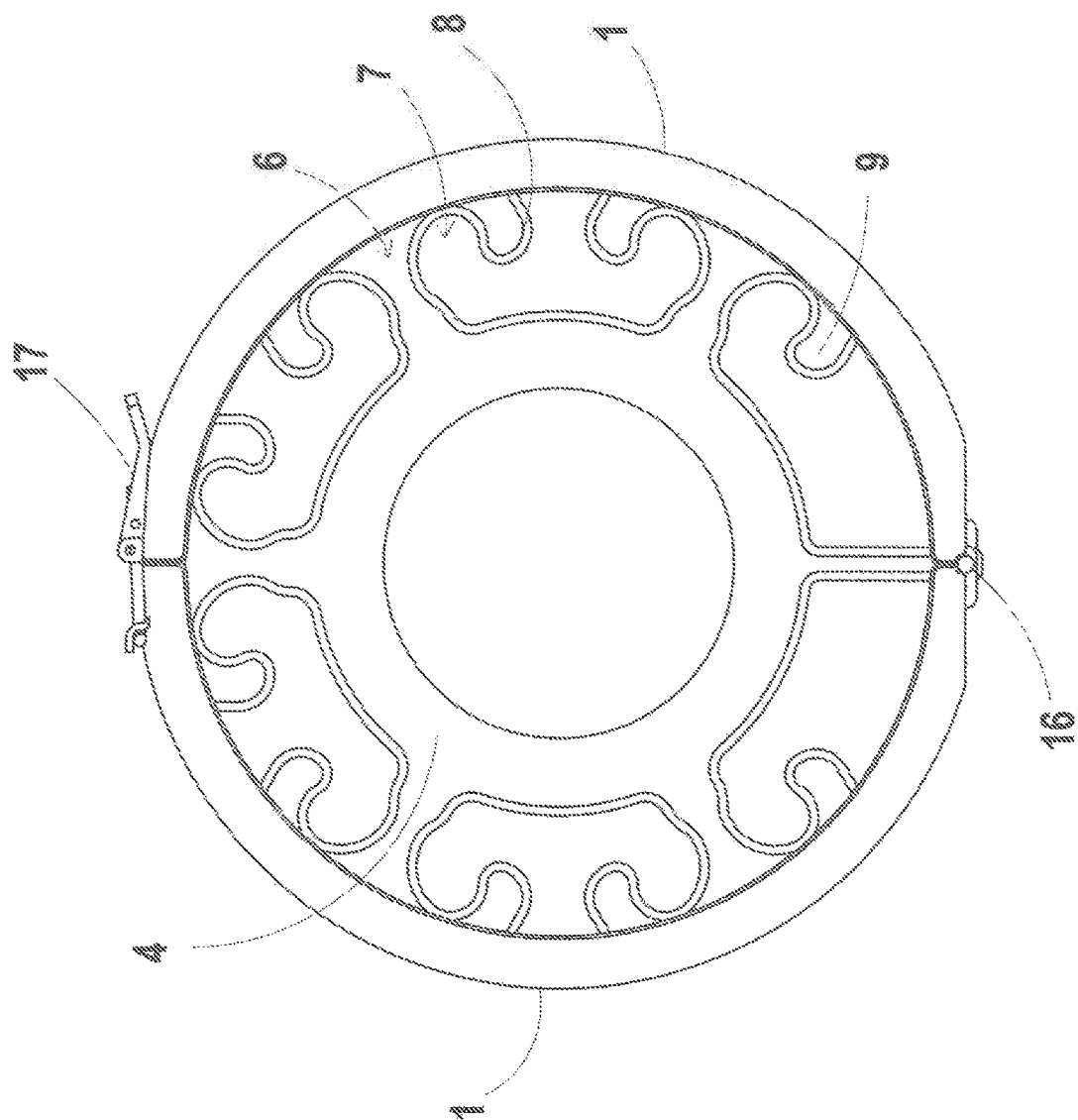
FIG. 9 is a side elevational view of the cable organizer of FIG. 8.

A cable organizer according to a first embodiment of the disclosure is shown in FIGS. 1-7. The first embodiment is shown in a perspective view in FIG. 1 in the general position that the device will assume while in use. FIG. 2 illustrates a side view of the device, with the latch 1 in the open position, as it would be prior to setting up the device for a surgery. The "organizer" may be secured to the surgical drape through a hook-and-loop fastener (e.g., Velcro™), or through a simple towel clamp, affixed to the drape and to the integral rings 2 and 3. The integral ring on the end 2 would typically be used when using the hook-and-loop fastener near the fenestrated portion of the laparoscopic drape or while conducting hysteroscopic surgery where the device would be used vertically and placed near the patient's midline. The center integral ring 3 may be used during laparoscopic cases, when the device is mounted horizontally to the mayo stand at the foot of the bed or in-between the intravenous poles at the head of the table. Surgeon's preference, type of case and position of the laparoscopic tower relative to the patient would influence a vertical or horizontal deployment.

As shown in FIGS. 1-7, the organizer body 4 is generally rectangular shaped and includes integral holders, which are essentially carvings or molded portions, along the bottom side 5. Each integral holder consists of one insertion slot 6 leading up to two resting surfaces 7 of sufficient size to accommodate laparoscopic tubes and cables. Each resting surface 7 is bounded by the integral holder wall 8 and by an inwardly tilted tooth 9 which extends above the plane of the resting surface and which retains and prevents cables from escaping through the insertion slot. Cables and tubes which are inserted through the insertion slot must negotiate an S shaped path before resting on the resting surface. This complex path also prevents cables from inadvertent escape. The cross-sectional area of the resting surface, integral holder wall and tooth each have a rounded, preferably circular, curvature 10 so as to maximize contact area with wires and tubes inserted into this space.

The inwardly tilted tooth and the slot each have rounded contours 11 to prevent cable chafing and ensure patient and surgeon safety. A rotating U-shaped latch 1, shown in FIG. 6, which is secured to the main body of the device 4 through a permanent fastener (such as a rivet) located at the pivot point 12, is then rotated into place, thus securing the cables by blocking all of the insertion slots FIG. 1. The latch itself is prevented from opening due to friction between itself and the main body of the device. Both of these parts have, at the level of the fastener, a friction ring consisting of radial grooves or raised portions 13 molded into the plastic and which increase friction FIG. 5.

In the disclosed embodiment, the organizer has a flat cross section, allowing it to remain flush with the surgical field, while the latch is U-shaped. The device may be dimensioned as desired, but the preferred dimensions are as follows: thickness: ¼ inch, total length: 10 inches, total width: 2.5 inches.

When in use, the load from the cables and tubes 20 which the integral holder supports and transfers to the entire device is relatively minimal, thus minimum strain is expected. This allows for relatively lightweight plastics and injection molded techniques to be used and for costs of manufacture to be relatively low.

A second embodiment of this device, which is substantially similar to a donut in appearance, is depicted in FIGS. 8-12. Similar to the device described previously, integral holders 5 are formed in a circular main body 4. As described previously, each integral holder consists of one insertion slot 6 leading up to two resting surfaces 7. Each resting surface is bounded by the integral holder wall 8 and by an inwardly tilted tooth 9 which extends above the plane of the resting surface preventing cables 20 from easily escaping through the insertion slot. The inwardly tilted tooth and the slot each have rounded contours. Additionally, the resting surface, integral holder wall and surface of the tooth all have a circular curvature to better grip the wires and tubes inserted into this space 10. Similar to the previously described embodiment, the central part of this embodiment consists of an integral ring 3, resembling a donut hole, allowing device to be secured to the surgical field (also known as the operating field, which is an isolated area where surgery is performed, and which is kept sterile by aseptic techniques such as drapes, curtains, or shields).

Figure 10:
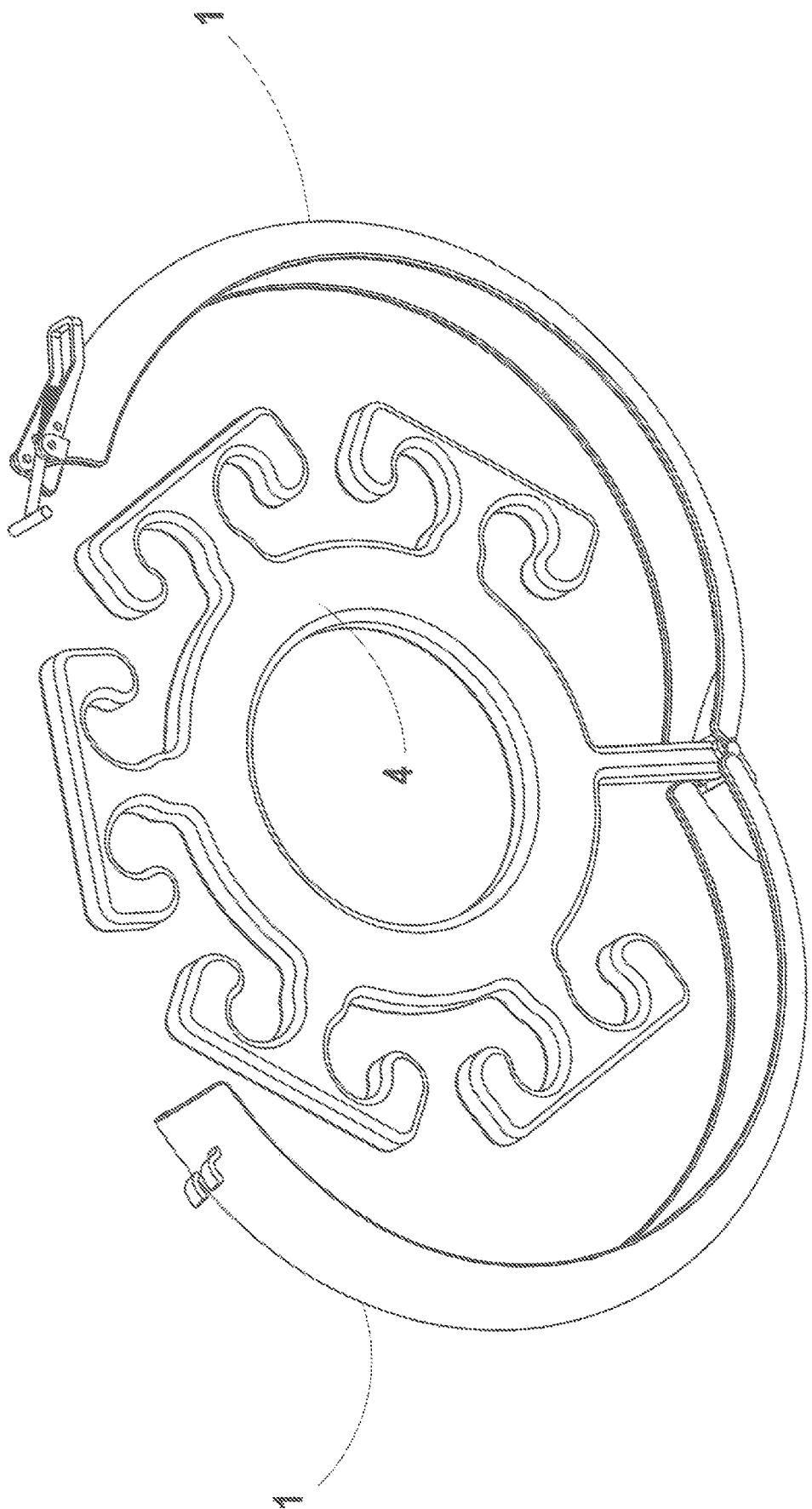
FIG. 10 is a top perspective view of the cable organizer of FIG. 8, the cable organizer shown with the latches opened.
Figure 11:
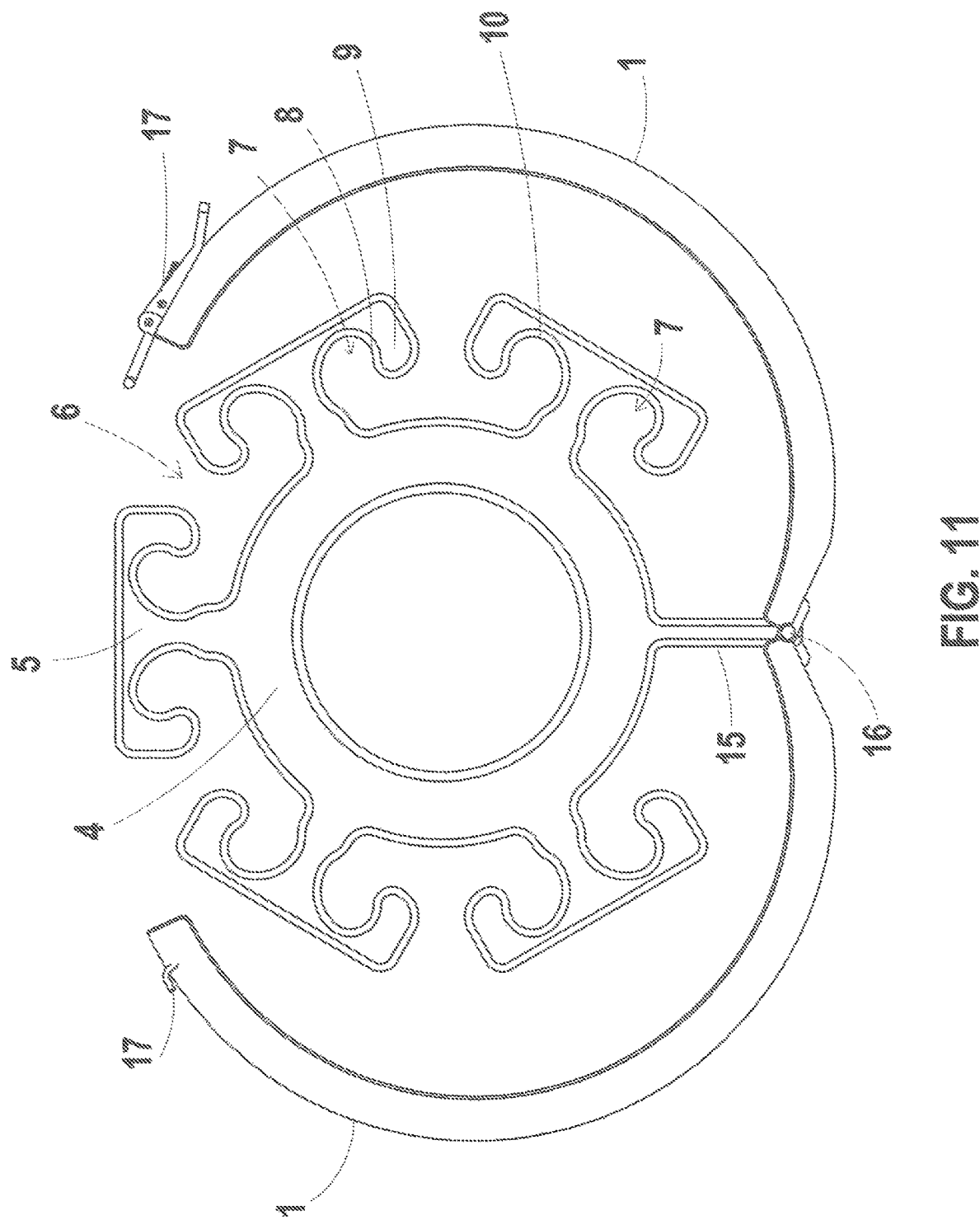
FIG. 11 is a side elevational view of the cable organizer of FIG. 10.
Figure 12:
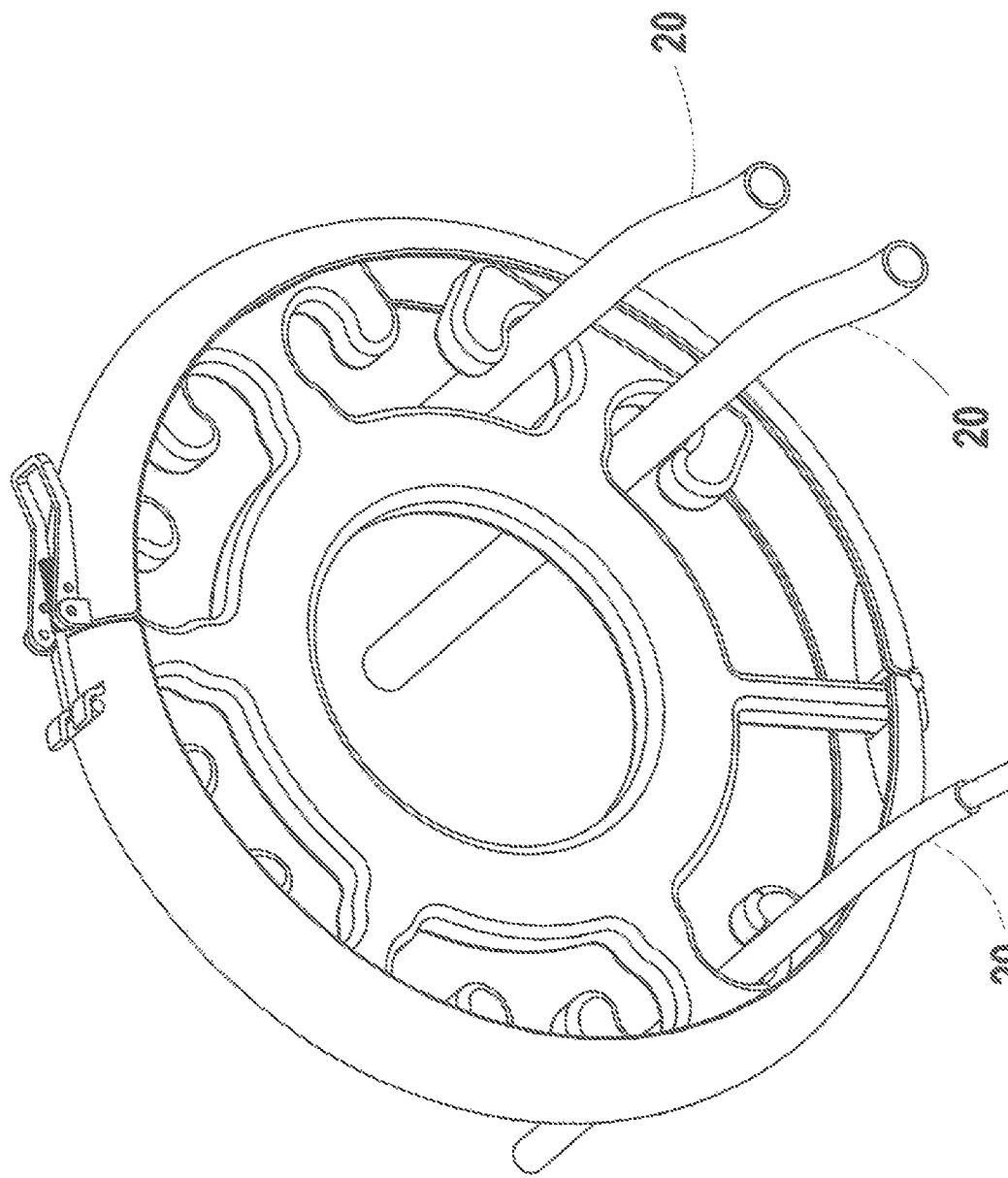
FIG. 12 is a top perspective view of the cable organizer of FIG. 9, the cable organizer shown in operation and securing cables.

The main body of this organizer is then encircled by a cylindrical latch 1. When secured, its inner surface rests flush against the integral holders and thus securing the cables by blocking all of the insertion slots 6. The cylindrical latch, secured to the main body by means of a radial support 15, it is constructed out of two separate halves, each having a slightly inwardly curved cross section, similar to a tire, as shown in FIGS. 10 and 11. A hinge 16 joins together the two half cylinders and the radial support allowing them to open and close about the end of the cylindrical latch. A cam latch catch mechanism 17 secures the cylindrical latch closed. The curvilinear cross section increases safety, by providing no sharp edges which may harm the patient, while allowing for a better fit around the main body.

Figure 13:
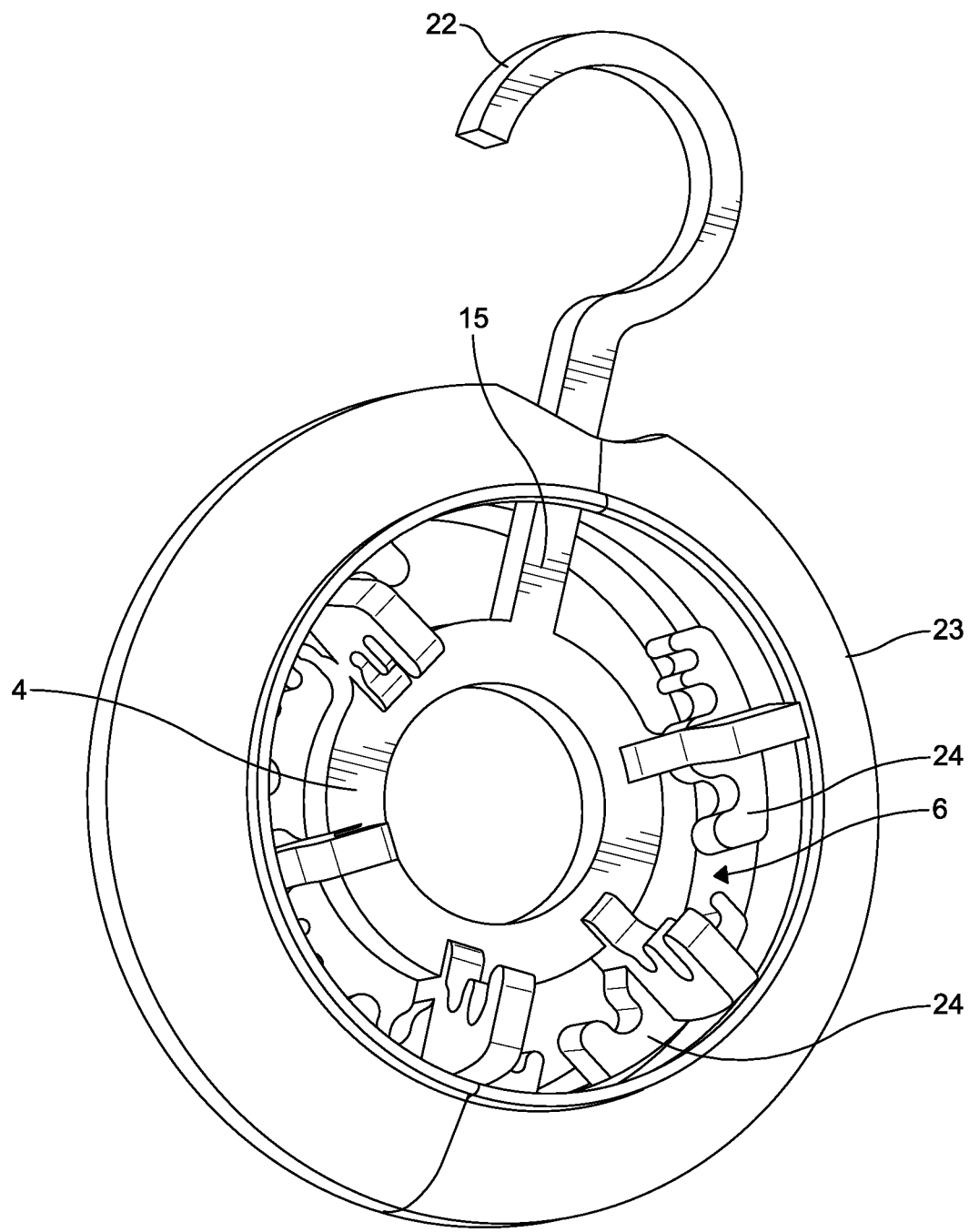
FIG. 13 is a top perspective view of a cable organizer according to another embodiment of the present disclosure, the cable organizer shown in a closed position.
Figure 14:
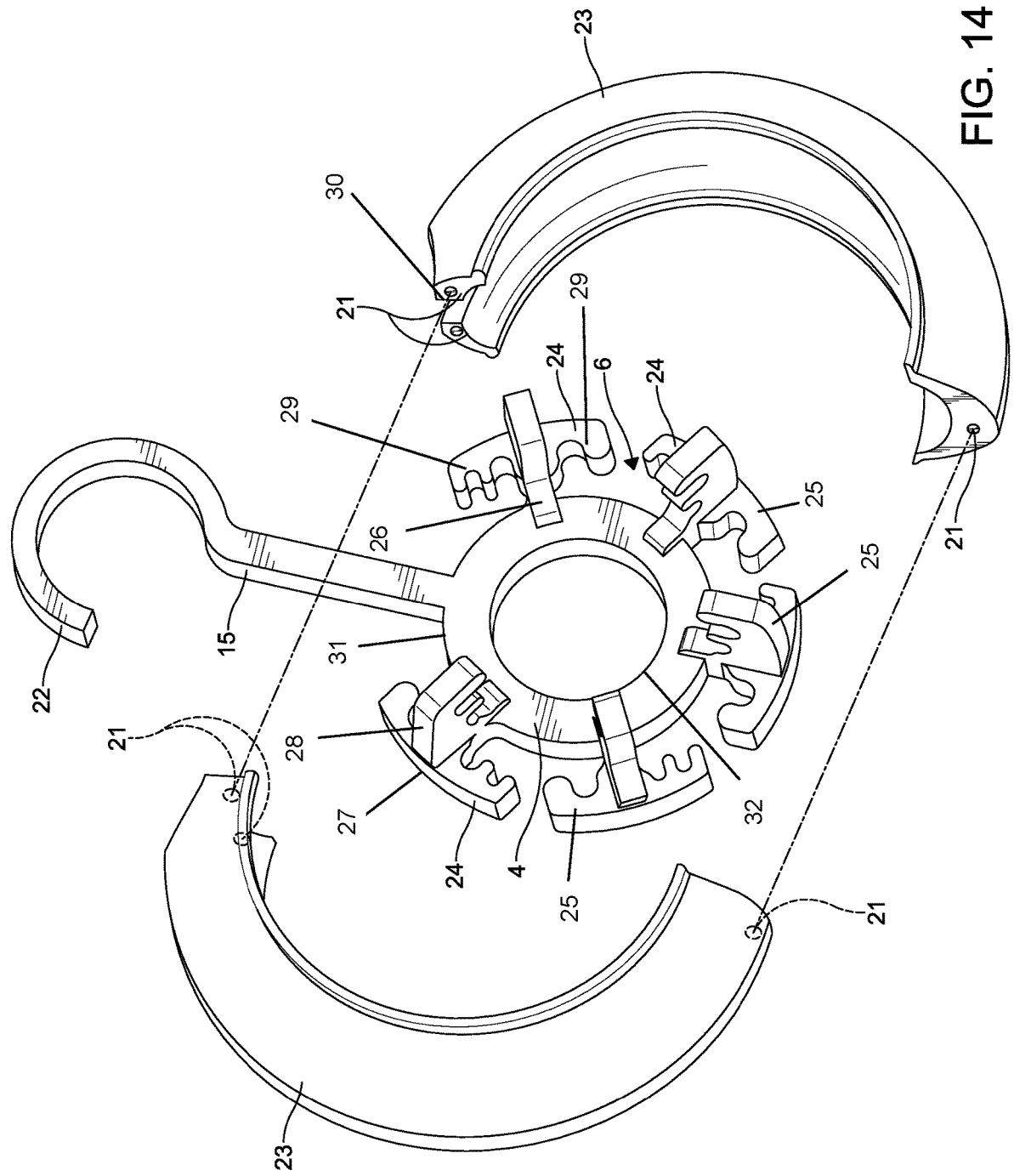
FIG. 14 is a top perspective view of the cable organizer of FIG. 13, the cable organizer shown in an opened position.
Figure 15:
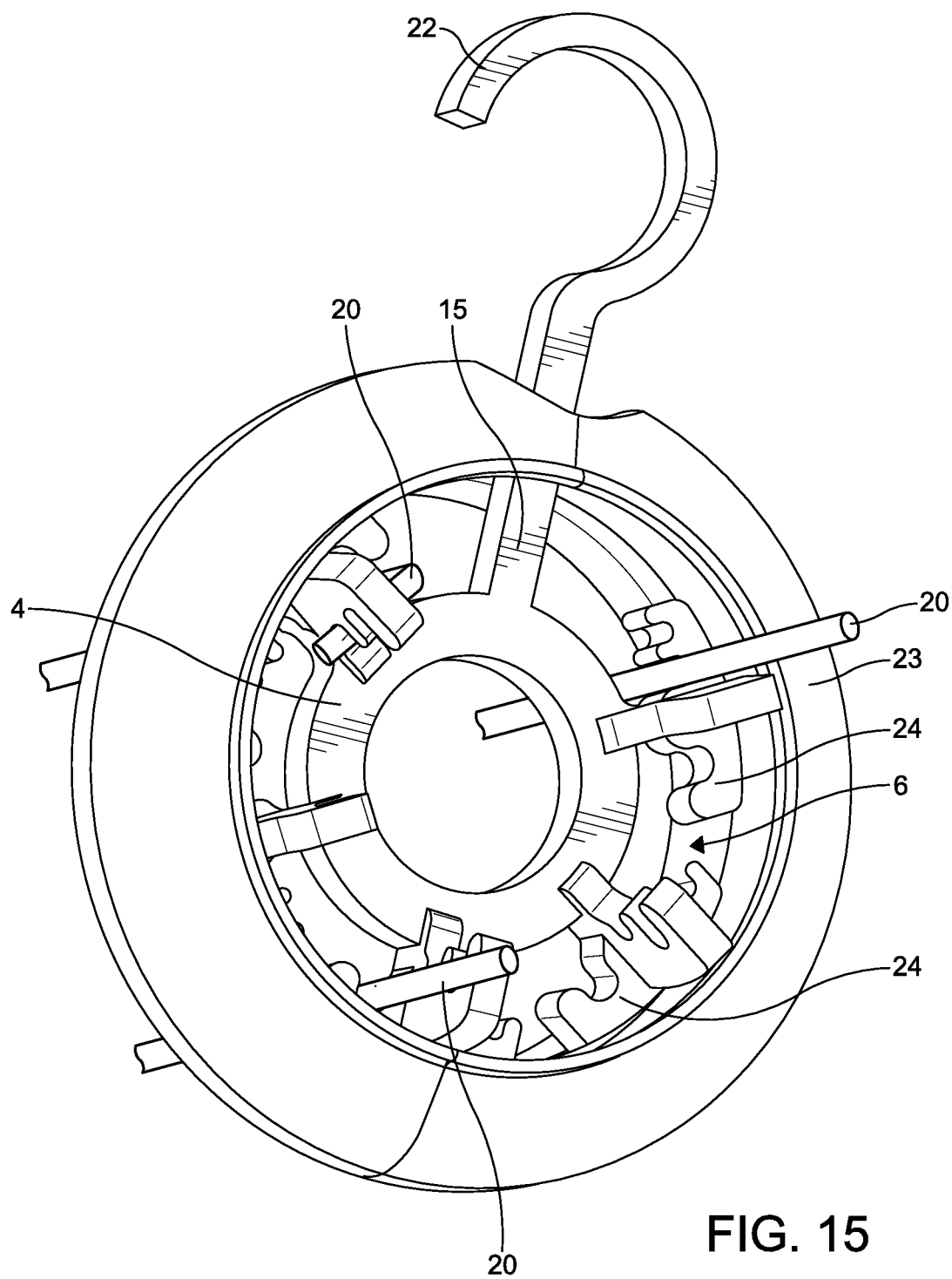
FIG. 15 is a top perspective view of the cable organizer of FIG. 13, the cable organizer shown in a closed position in operation and securing cables.

In a further embodiment shown in FIGS. 13-15, the organizing device has a plurality of integral holders 24 which allows for passing of the tube, wire, or cable 20 through the organizing device. The integral holders 24 may also permit for an angling or orienting of the tube, wire, or cable 20 in a different direction. The device is comprised of a substantially donut shaped body. The donut shaped body has a central integrated ring. The central integrated ring is hollow, and integrally molded in the main body of the device. The hollow portion 32 of the central integrated ring is capable of accepting hook-and-loop fastener (e.g., Velcro™) tabs, surgical towel clamps, or other means of securing the device to the surgical field.

In a particular embodiment, each of the integral holders 24 has a pair of generally T-shaped holder bodies that are combined and define four prongs 25. More particularly, the holder body has four prongs 25 that are defined by a vertical bar 26 depending from an outer perimeter 31 of the central integrated ring, a first horizontal bar 27 disposed on an end of the vertical bar 26, and a second horizontal bar 28 disposed on the end of the vertical bar 26 and oriented generally perpendicular with the first horizontal bar 27. The prongs 25 further have slots 29 that define resting surfaces for the tube, wire, or cable 20 as described further herein. The integral holders 24 may have a plurality of differently sized slots 29 configured to accommodate various sizes of the tubing, wiring, or cable 20.

The main body 4 and the integral holders 24 are selectively encapsulated or circumscribed by a cover 23. The cover 23 has curved surfaces for a better fit and safety. The cover 23 further has two half units, which when attached define the cover 23. Each of the half units has a slightly inwardly curved cross section, similar to a tire, as shown in FIG. 14.

As shown in FIGS. 13 and 14, the half units of the cover 23 may be selectively attached by a plurality of recessed magnets 21. The recessed magnets 21 may be disposed at ends of the half units of the cover 23. The ends of the half units of the cover 23 may also have channels 30 that are configured to receive the radial support 15 when in the close position, as described further hereinbelow. It should be appreciated that, with the use of the recessed magnets 21, there is no need for a hinge to lock the latch.

When the cover 23 is in the closed position on the main body 4, thereby encapsulating or circumscribing the main body 4 and the integral holders 24, the cover 23 rests flush against the integral holders 24. This in turn blocks all of the insertion slots 6 against a lateral insertion or removal of cables tubes and wires, 20, and thereby securing the cables, tubes, and wires 20 within the integral holders 24 of the main body 4.

With continued reference to FIGS. 13-15, the radial support 15 extends further beyond the cover 23. Furthermore, the radial support 15 may have a hook structure 22 formed at the end of the radial support 15. The hook structure 22 may allow the organizing device to be attached to a pole or operating bed if needed. This hooking capability increases the safety of the entire unit to militate against displacement from the desired location of the organizing device.

Thus, the present disclosure provides a minimally invasive surgical cable organizer that may be used in a laparoscopic or hysteroscopic setting and which fulfills the objects of the invention. In all embodiments, the device is all essentially one-piece and has no separable parts (such as screws) which may be removed and lost in a patient's body.

While the invention is described in specific embodiments, many alternatives, modifications and variations, which will be apparent to those skilled in the art, fall within the spirit and scope of the claims.

What is claimed is:

1. An organizing device for use during a medical procedure, comprising:
   a main body including a central integrated ring with an outer perimeter and a plurality of integral holders radially arranged around the outer perimeter of the integrated ring and configured to secure at least one of a cable, a wire, and a tube during the medical procedure, each of the integral holders defined by a holder body depending from the central integrated ring, the main body further configured to be secured to a surgical field; and
   a cover separable removably disposed on the main body and defined by a pair of half units, each of the half units having at least one magnet attached to an end of each of the half units and configured to selectively hold the half units in a closed position on the main body, and configured to permit for a manual separation of the half units into an opened position,
   wherein the central integrated ring has a hollow portion, and
   wherein the central integrated ring further has a radial support that passes through a channel in the cover, the radial support having a hook structure formed at an end of the radial support for further securement of the device to the surgical field.

2. The organizing device of claim 1, wherein the hollow portion of the central integrated ring is an attachment means configured to accept at least one of hook-and-loop fastener tabs and surgical towel clamps for securing the device to the surgical field.

3. The organizing device of claim 1, wherein the at least one magnet is disposed adjacent the channel in each of the half units of the cover.

4. The organizing device of claim 1, wherein the each of the half units of the cover has an arcuate shape permitting a flush fit against the integral holders when in the closed position.

5. The organizing device of claim 1, wherein the main body has no separable parts.

6. The organizing device of claim 1, wherein the main body is donut shaped.

7. An organizing device for use during a medical procedure, comprising:
   a main body including a central integrated ring with an outer perimeter and a plurality of integral holders radially arranged around the outer perimeter of the integrated ring and configured to secure at least one of a cable, a wire, and a tube during the medical procedure, each of the integral holders defined by a holder body depending from the central integrated ring, the main body further configured to be secured to a surgical field; and
   a cover separable removably disposed on the main body and defined by a pair of half units, each of the half units having at least one magnet attached to an end of each of the half units and configured to selectively hold the half units in a closed position on the main body, and configured to permit for a manual separation of the half units into an opened position, wherein the holder body has four prongs that are defined by a vertical bar depending from the central integrated ring, a first horizontal bar disposed on an end of the vertical bar, and a second horizontal bar disposed on the end of the vertical bar and oriented generally perpendicular with the first horizontal bar.

8. The organizing device of claim 7, wherein the horizontal bars of the holder body further have a plurality of slots which are configured to selectively retain the at least one of the cable, the tube, and the wire.

9. The organizing device of claim 8, wherein the plurality of slots are different sizes configured to selectively retain different sizes of at least one of the cable, the tube, and the wire.

* * * * *